US012334195B2

United States Patent
Kishimoto et al.

(10) Patent No.: US 12,334,195 B2
(45) Date of Patent: Jun. 17, 2025

(54) OPTIMIZATION OF MULTIPLE MOLECULES

(71) Applicant: INTERNATIONAL BUSINESS MACHINES CORPORATION, Armonk, NY (US)

(72) Inventors: Akihiro Kishimoto, Tokyo (JP); Toshiyuki Hama, Tokyo (JP); Hsiang Han Hsu, Kanagawa (JP); Djallel Bouneffouf, Wappinger Falls, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 828 days.

(21) Appl. No.: 17/559,595

(22) Filed: Dec. 22, 2021

(65) Prior Publication Data

US 2023/0197208 A1 Jun. 22, 2023

(51) Int. Cl.
*G16C 20/70* (2019.01)
*G16C 20/10* (2019.01)
*G16C 20/20* (2019.01)
*G16C 60/00* (2019.01)

(52) U.S. Cl.
CPC ............. *G16C 20/70* (2019.02); *G16C 20/10* (2019.02); *G16C 20/20* (2019.02); *G16C 60/00* (2019.02)

(58) Field of Classification Search
CPC ........ G16C 20/70; G16C 20/20; G16C 20/10; G16C 60/00
See application file for complete search history.

(56) References Cited

U.S. PATENT DOCUMENTS

2021/0125691 A1   4/2021  Wlodarczyk-Pruszynski et al.
2022/0383993 A1*  12/2022  Yoo .................. G16C 20/60

FOREIGN PATENT DOCUMENTS

CA        2166397 C  *  3/2000  .......... B01J 19/0046

OTHER PUBLICATIONS

Chen et al., "A Deep Generative Model for Molecule Optimization via One Fragment Modification", arXiv:2012.04231v4 [cs.LG] Nov. 15, 2021, pp. 1-33.

(Continued)

*Primary Examiner* — Elias Desta
(74) *Attorney, Agent, or Firm* — Tutunjian & Bitetto, P.C.; Robert Richard Aragona

(57) ABSTRACT

A computer implemented method of modifying molecular structures constrained by a budget is provided. The computer implemented method includes receiving from a user a subset of molecules, where each molecule is represented as a generation path, and receiving from the user an allotted budget for modifying a selection of molecules from the subset of molecules. The computer implemented method further includes testing a first molecule, and reducing the allotted budget based on the resources expended to test the first molecule. The computer implemented method further includes testing a second molecule, and reducing the allotted budget based on the resources expended to test the second molecule. The computer implemented method further includes determining a remaining amount of the allotted budget, and testing additional molecules from the subset of molecules until the allotted budget is exhausted. The computer implemented method further includes presenting the tested molecules to the user.

20 Claims, 5 Drawing Sheets

(56) References Cited

OTHER PUBLICATIONS

Hartke et al., "McKay's Canonical Graph Labeling Algorithm", Contemporary Mathematics, vol. 479, Feb. 2009, pp. 1-12.
Harvey et al., "Limited Discrepancy Search", In IJCAI (1) Aug. 20, 1995, pp. 607-615.
Hiroshi Kajino, "Molecular Hypergraph Grammar with Its Application to Molecular Optimization" In International Conference on Machine Learning May 24, 2019 (pp. 3183-3191). PMLR.
Brendan McKay, "Isomorph-Free Exhaustive Generation", Journal of Algorithms, Feb. 1, 1998, pp. 306-324.
Takeda et al., "Molecular Inverse-Design Platform for Material Industries", In Proceedings of the 26th ACM SIGKDD International Conference on Knowledge Discovery & Data Mining, Aug. 23, 2020 (pp. 2961-2969).
Xia et al., "Thompson Sampling for Budgeted Multi-armed Bandits", In Twenty-Fourth International Joint Conference on Artificial Intelligence, Jun. 27, 2015, pp. 3960-3966.
You et al., "Graph Convolutional Policy Network for Goal-Directed Molecular Graph Generation", 32nd Conference on Neural Information Processing Systems (NeurIPS 2018), Jun. 7, 2018, pp. 1-12.
Perez et al., "AdaptiveBandit: A multi-armed bandit framework for adaptive sampling in molecular simulations", arXiv:2002.12582v1 [physics.comp-ph] Feb. 28, 2020, pp. 1-24.
Gani et al., "Computer-Aided Molecular Design and Property Prediction", In Computer Aided Chemical Engineering, Jan. 1, 2016 (vol. 39, pp. 153-196).
Michael A. Gonzalez, "Introduction to Green and Sustainable Chemistry", In Encyclopedia of Sustainable Technologies, vol. 3, Jul. 14, 2017, pp. 487-495.
Authors et al., Disclosed Anonymously, "Molecule Design with Desired Components", IP.com No. PCOM000265543D, Apr. 23, 2021, pp. 1-4.
Takeda et al., "Molecule Generation Experience: An Open Platform of Material Design for Public Users", arXiv preprint arXiv:2108.03044. Aug. 6, 2021, pp. 1-10.

* cited by examiner

OPTIMIZATION OF MULTIPLE MOLECULES

BACKGROUND

The present invention generally relates to a chemical modification tool, and more particularly to a chemical modification tool that optimizes molecules.

The multi-armed bandit problem models an agent that simultaneously attempts to acquire new knowledge (called "exploration") and optimize their decisions based on existing knowledge (called "exploitation"). The problem requires balancing reward maximization based on the knowledge already acquired with attempting new actions to further increase knowledge. The bandit problem is formally equivalent to a one-state Markov decision process, where the regret after N rounds is defined as the expected difference between the reward total associated with an optimal strategy and the sum of the actual collected rewards.

SUMMARY

In accordance with an embodiment of the present invention, a computer implemented method of modifying molecular structures constrained by a budget is provided. The computer implemented method includes receiving from a user a subset of molecules, where each molecule is represented as a generation path, and receiving from the user an allotted budget for modifying a selection of molecules from the subset of molecules. The computer implemented method further includes testing a first molecule, and reducing the allotted budget based on the resources expended to test the first molecule. The computer implemented method further includes testing a second molecule, and reducing the allotted budget based on the resources expended to test the second molecule. The computer implemented method further includes determining a remaining amount of the allotted budget, and testing additional molecules from the subset of molecules until the allotted budget is exhausted. The computer implemented method further includes presenting the tested molecules to the user.

In accordance with another embodiment of the present invention, a computer system for modifying molecular structures constrained by a budget is provided. The computer system includes one or more processors, a computer display, and a computer memory operatively coupled to the one or more processors. The computer system further includes a chemical modification tool stored in the computer memory that is configured to receive from a user a subset of molecules, where each molecule is represented as a generation path. The chemical modification tool is further configured to receive from the user an allotted budget for modifying a selection of molecules from the subset of molecules. The chemical modification tool is further configured to test a first molecule, and reduce the allotted budget based on the resources expended to test the first molecule. The chemical modification tool is further configured to test a second molecule, and reduce the allotted budget based on the resources expended to test the second molecule. The chemical modification tool is further configured to determine a remaining amount of the allotted budget, and test additional molecules from the subset of molecules until the allotted budget is exhausted. The chemical modification tool is further configured to present the tested molecules to the user on the computer display.

In accordance with yet another embodiment of the present invention, a computer program product for modifying molecular structures constrained by a budget is provided. The computer program product for modifying molecular structures constrained by a budget includes program instructions executable by a processor to cause a computer to receive from a user a subset of molecules, where each molecule is represented as a generation path, and receive from the user an allotted budget for modifying a selection of molecules from the subset of molecules. The computer program product can further cause a computer to test a first molecule, and reduce the allotted budget based on the resources expended to test the first molecule. The computer program product can further cause a computer to test a second molecule, and reduce the allotted budget based on the resources expended to test the second molecule. The computer program product can further cause a computer to determine a remaining amount of the allotted budget, and test additional molecules from the subset of molecules until the allotted budget is exhausted. The computer program product can further cause a computer to present the tested molecules to the user on a computer display.

These and other features and advantages will become apparent from the following detailed description of illustrative embodiments thereof, which is to be read in connection with the accompanying drawings.

BRIEF DESCRIPTION OF THE DRAWINGS

The following description will provide details of preferred embodiments with reference to the following figures wherein.

DETAILED DESCRIPTION

Embodiments of the present invention provide a tool for generating new molecular structures having targeted values for physical and/or chemical properties. The molecular structures can be generated from scratch, where over 1000 structures can be generated for a user. However, not all generated molecular structures are of interest to the user.

A subset of the generated molecular structures that are of interest may be selected for optimization by a user. Molecular optimization, however, can be a time-consuming task. If the user selects many molecules, all of the molecules may not be able to be sufficiently optimized in a limited amount of time and with limited computer resources. Therefore, given a fixed amount of time (e.g., 1 hour), more time resources can be allocated to test and optimize the more promising molecules; however, which molecular structures will provide the best target properties would generally be unknown at the initial time of selection.

Embodiments of the present invention provide a chemical modification tool, and more particularly to a chemical modification tool that tests and optimizes molecules, and operates within a user-defined budget. The chemical modification tool (i.e., the tool) can automatically determine which of the molecules should be optimized, where the user specifies the budget (e.g., time limit). A multi-armed bandit approach can be used to determine which of the molecules should be tested and optimized.

In various embodiments, a subset of the generated molecular structures can be selected by the user for optimization. The selected molecular structures represented as a generation path can be modified to obtain property values closer to specified target values provided by a user. Modification can include simplification of complicated structures in the subset. The number of modifications can be regarded as a distance from the original molecular structure and used as a similarity measure.

Embodiments of the present invention provide a molecule generation path, where a sequence of adding operations of building blocks (e.g., atoms, rings, and sub-graphs) can be uniquely determined for a molecular structure. A molecular structure can be generated that satisfies a feature vector characterizing a given molecule by using a canonical construction algorithm.

In various embodiments, a budget (e.g., time limit, computer resource limit, etc.) and an objective function to be maximized or minimized can be selected or inputted into the tool.

Exemplary applications/uses to which the present invention can be applied include, but are not limited to: computational material discovery tools.

It is to be understood that aspects of the present invention will be described in terms of a given illustrative architecture; however, other architectures, structures, materials and process features and steps can be varied within the scope of aspects of the present invention.

Figure 1:
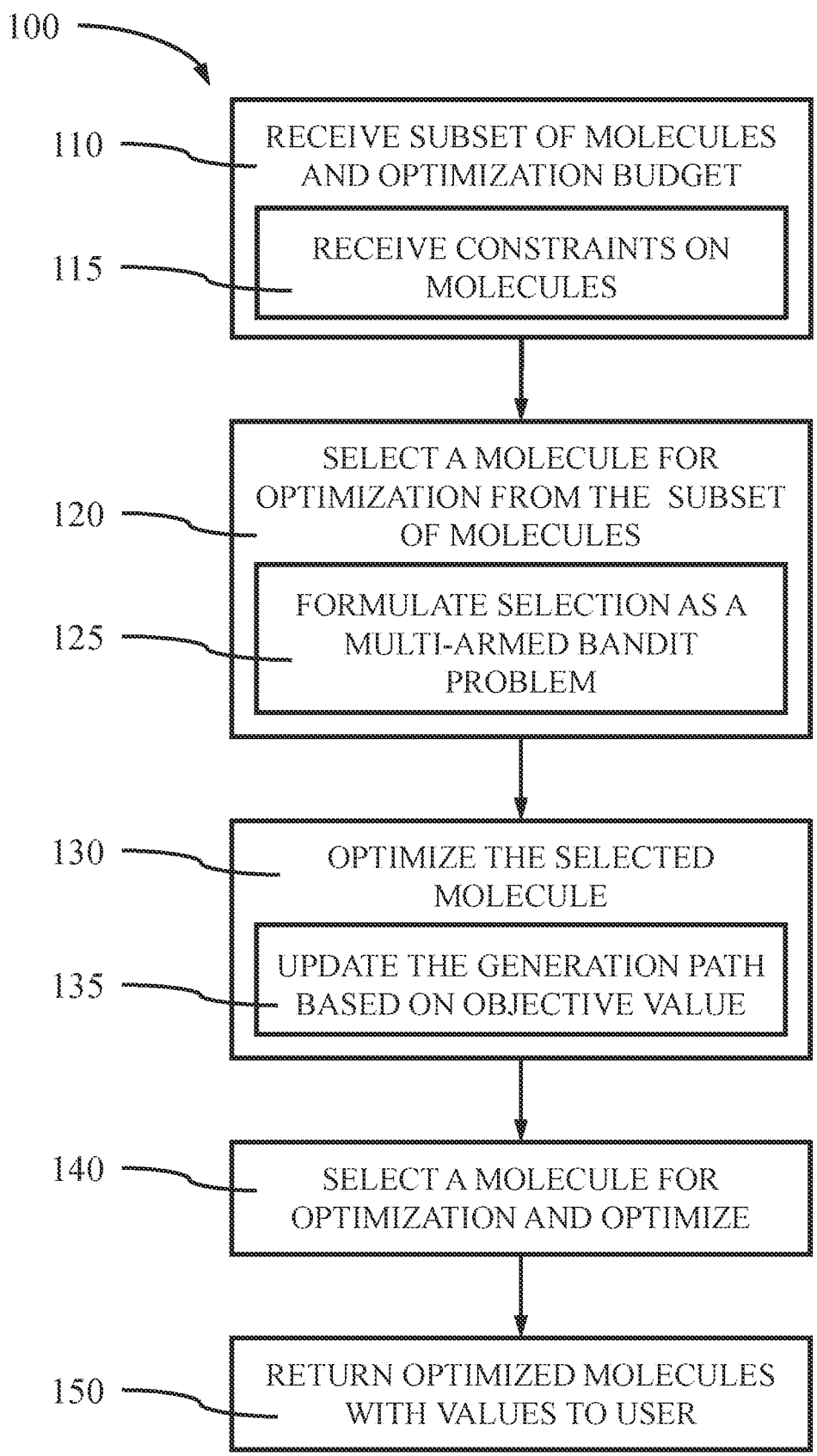
FIG. 1 is a block/flow diagram showing a system/method of molecular optimization for multiple molecules under a limited budget, in accordance with an embodiment of the present invention.

Referring now to the drawings in which like numerals represent the same or similar elements and initially to FIG. 1, FIG. 1 is a block/flow diagram showing a system/method of molecular optimization for multiple molecules under a limited budget, in accordance with an embodiment of the present invention.

In various embodiments, a chemical modification tool 100 that optimizes molecules under the constraints of a limited budget can test molecular structures included in a subset and provide optimized molecules relating to a chemical, physical, or biological property identified by a user.

At block 110, the modification tool can receive a subset of molecular structures selected by a user from a larger set of generated molecular structures. The larger set of generated molecular structures could have been previously generated by a molecular generation algorithm. In various embodiments, the set of generated molecular structures can have at least 1000 molecular structures, and the subset may have at least 25 molecules, at least 50 molecules, or at least 100 molecules. Each generated molecular structure can have a corresponding unique generation path. The generation path can involve an adding operation. The modification tool can be configured to receive and operate on these unique generation paths.

In one or more embodiments, a sequence of molecules to be tested and optimized, a budget, ranges of property values, and an objective function to maximize or minimize can be provided to the tool.

An optimization budget can be received with the selected subset of molecular structures, where the optimization budget can specify, for example, a duration or time limit, an amount of computer processing power, or a total number of modifications, to be utilized for the optimization of all the selected molecular structures.

In various embodiments, an objective function can also be identified for use in the optimization process, where the objective function can be, for example, a Ridge Regression model or a Support Vector Regression model which has been trained by a list of pairs each of which consists of a molecule represented as simplified molecular-input line-entry system (SMILES), which is a specification in the form of a line notation for describing the structure of chemical species, and a numerical value for a target property (such as toxicity, glass transition temperature, bioavailability, etc.). The number of modifications can be regarded as a distance from the original molecular structure and used as a similarity measure.

At block 115, the user can specify constraints on the allowable modifications to the selected molecular structures, where the user can identify, for example, atoms, rings, pendant moieties, and sub-graphs/sub-structures that should be retained by the molecular structure during a modification process. The user can also identify constraints, such as chemical sub-structures to include and/or exclude for modifying and optimizing the molecule structure. For example, if a user marks sub-structures (e.g., active parts) of the selected molecules and give them as structural constraints, the modification tool can optimize the molecules while satisfying the constraints (e.g., simplifying only supporting sub-structures).

At block 120, the tool can test a particular molecule from the subset of molecular structures selected by the user by selecting a particular molecular structure from the subset, modifying the selected molecular structure, and determining whether the modification improves a chemical, physical, or biological property of the molecule. Testing can include selecting a molecule from the subset of molecular structures, modifying the selected molecular structure, and determining whether the modified structure has a chemical, biological, and/or physical characteristic or property closer to a user defined value. The tool can identify one of the plurality of selected molecular structures that can be modified in a manner believed to improve chemical, biological, and/or physical characteristics and properties of the molecular structure. Optimizing a molecular structure represented as a generation path to have an improve chemical, biological, and/or physical characteristic or property involves modifying the molecular structure in a manner that changes the value of the chemical, biological, and/or physical characteristic or property of the molecular structure to be closer to a user defined value.

At block 125, the tool can use a multi-armed bandit approach to select from the subset of molecular structures a first molecular structure and a sequence of subsequent molecular structures to be modified, where the selection process of the subsequent structures can also be formulated as a multi-armed bandit problem. An allotted budget receiving from the user can be used for optimizing a selection of molecules from the subset of molecules, where the number of selected molecules can be the same as or less than the number of molecular structures in the subset. The tool can iteratively select and optimize molecular structures until the allotted budget (e.g., time, computing power, etc.) is exhausted.

At block 130, the first molecular structure is selected for modification and evaluation against the specified target values for the specified chemical, biological, and/or physical characteristics and properties of the molecular structure.

In various embodiments, a generation path can be modified, corresponding to optimizing a molecule. Modifications can be inserting, deleting, and replacing components of the generation path. In various embodiments, molecular structures can be generated from modified generation paths and evaluated according to the given objective function, for example, a Ridge regression model trained with 1000 examples.

At block 135, the generation path corresponding to the selected molecular structure can be updated to show the modification that improves the objective value generated by the objective function. The generation path can be maintained within a threshold of the associated similarity measure to attempt to obtain a molecule that has a better objective value. The similarity measure can include the constraints selected by the user for the molecular structure. The allotted budget can be reducing based on the resources expended to optimize the selected molecule, update the generation path, and calculate the objective value.

In various embodiments, a number of modification attempts determined as part of the multi-armed bandit approach can be applied to and evaluated for the selected molecular structure.

The total number of modifications can be constrained by the allotted budget, such that not all molecules in the subset may be optimized, or not all selected molecules are sufficiently optimized before the budget is exhausted.

At block 140, another molecular structure can be selected for optimization from the subset. A molecule to be optimize next can be selected from the sequence of molecules based on the budget or remaining budget. In various embodiments, each of the subset of molecular structures can be modified through selection and modification until the allotted budget has been used up.

At block 150 the final values generated for each of the optimized molecules can be presented to the user. The subset of optimized molecules can be presented in an ordered manner based on each of their objective values. The order can be a decreasing ordered based on the objective value of each optimized molecule.

Figure 2:
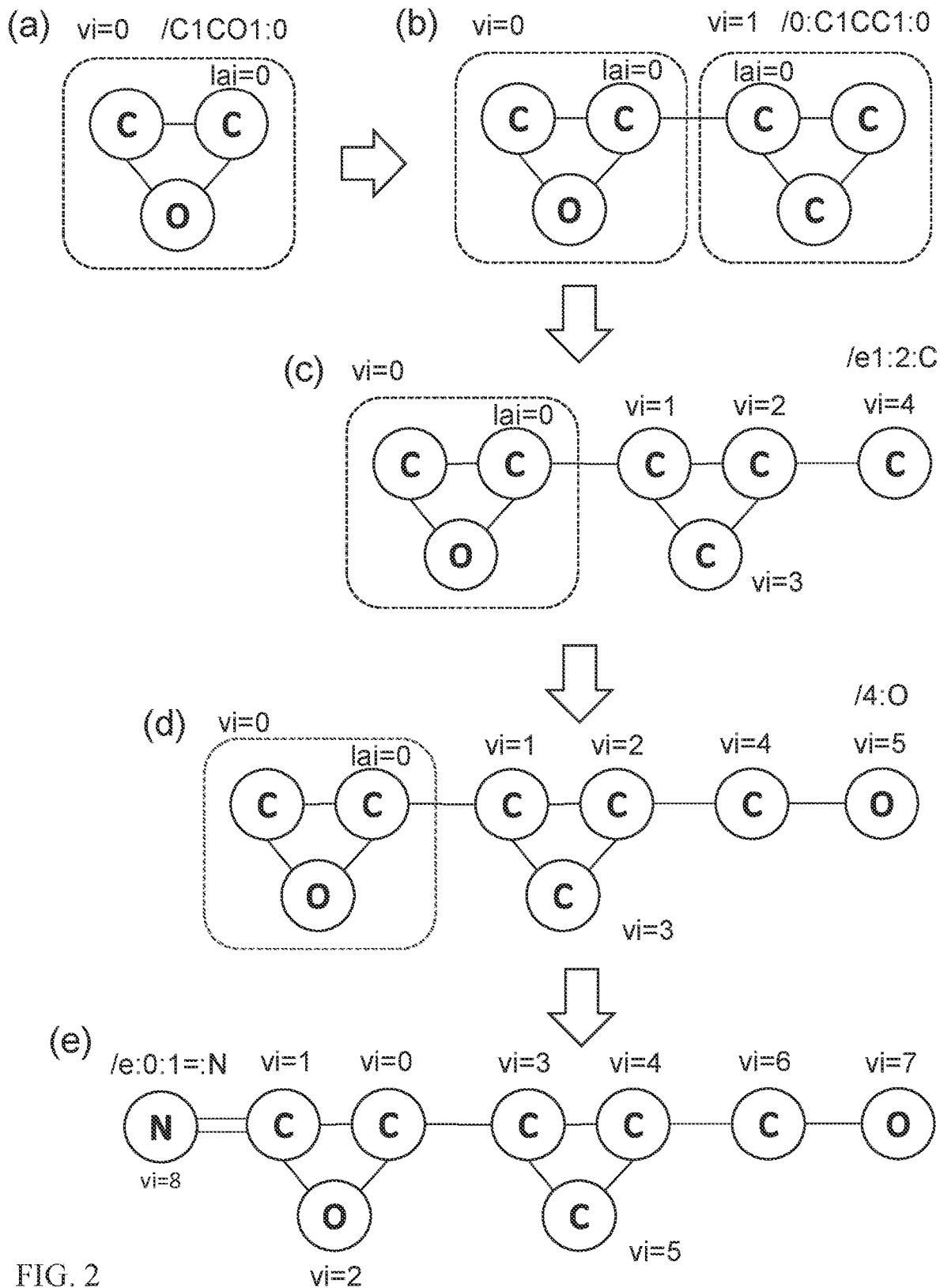
FIG. 2 is a flow diagram showing a series of operations for constructing a generation path, in accordance with an embodiment of the present invention.

FIG. 2 is a flow diagram showing a series of operations for constructing a generation path, in accordance with an embodiment of the present invention.

In one or more embodiments, a generation path is a sequence of operations, where for example, each operation is represented as "/[edd:][ff(=#):]SMILES[:gg]", where dd, ff, and gg are numbers and SMILES is a molecule substructure in SMILES format. Depending on the operation, the components shown inside the brackets may not be present. Therefore, (=#) indicates that either nothing, "=" or "#" appears in the operation, where " " corresponds to a single bond, the "=" corresponds to a double bond, and the "#" corresponds to a tripe bond, connecting two atoms. There are two kinds of indexes in the operation: one called a vertex index (dd and ff) for indexing either a substructure (e.g., ring) or an atom, and the other called a local atom index for indexing within a substructure (for gg). There are two cases where a vertex index is assigned. One case is where a vertex index, which is unique in the entire graph, is assigned to an atom. The other case is where a vertex index, which is unique in the entire graph, is assigned to a set of atoms for a substructure R. Assume that R has a vertex index dd. When R is expanded by an operation with the "edd" component which represents an expansion of the substructure with vertex index dd (i.e., substructure R), the vertex index dd for R is removed and a unique vertex index is assigned to each atom in R. On the other hand, the local atom index has a unique predefined number only within R. If R has not been expanded yet, the local atom index indicates that its corresponding atom is the only one in R allowed to be connected to another atom outside R. The vertex index ff indicates its corresponding atom/structure is connected to SMILES in the current operation.

SMILES (Simplified Molecular Input Line Entry System) is a chemical notation that allows a user to represent a chemical structure in a way that can be used by the computer. By combining atomic symbols and bond symbols simple chain structures can be represented. The structures in SMILES are represented without showing hydrogen atoms. An atom is represented using its respective atomic symbol. Upper case letters refer to non-aromatic atoms; lower case letters refer to aromatic atoms. If the atomic symbol has more than one letter the second letter must be lower case.

Bonds are denoted as: no symbol for single bond (e.g., CC for ethane); "=" for double bond (e.g., C=C for ethene); "#" for triple bond (e.g., C#N for hydrocyanic acid); and "." for disconnected/salt structure (e.g., Na·Cl).

A branch from a chain is specified by placing the SMILES symbol(s) for the branch between parenthesis. The string in parentheses is placed directly after the symbol for the atom to which it is connected. If it is connected by a double or triple bond, the bond symbol immediately follows the left parenthesis.

SMILES allows a user to identify ring structures by using numbers to identify the opening and closing ring atom. For example, in C1CCCCC1, the first carbon has a number '1' which connects by a single bond with the last carbon which also has a number '1'. The resulting structure is cyclohexane.

In a non-limiting example, /C1CO1:0/0:C1CC1:0/e1:2:C/4:O/e0:1=:N is a sequence of operations, leading to construct O1C(=N)C1C2C(CO)C2 in FIG. 2. Where, "/C1CO1:0" generates "C1CO1", at operation (a), which is not yet expanded. Vertex index 0 is assigned to "C1CO1" with local atom index 0 for one carbon C. Unless "C1CO1" is expanded, "C" of local atom index 0 is the only one allowed to connect to an additional structure. In the second operation at (b), "/0:C1CC1:0" generates unexpanded "C1CC1" to which vertex index 1 is assigned. One carbon "C" in "C1CC1" has local atom index 0 stemming from the second "0" in "/0:C1CC1:0". The first "0" in "/0:C1CC1:0" indicates C1CC1 should be connected to the substructure with vertex index 0 (i.e., C1CO1). Since these two substructures are unexpanded, the two atoms with local atom indexes are connected with a single bond with each other in (b). In the third operation at (c), "/e:1:2:C" indicates the structure of graph index 1 (i.e. C1CC1) is expanded, "e". In the expansion, the vertex index 1 for C1CC1 is removed and each of their atoms has its own vertex index 1, 2 or 3 unique in the entire graph. Then, a new carbon C to which vertex index, $v_i=4$ is assigned is connected to an atom of vertex index, $v_i=2$ (i.e. C in C1CC1) with a single bond in (c). In the fourth operation at (d), "/4:O" connects "C" of vertex index, $v_i=4$ to an oxygen "O" to which vertex index, $v_i=5$ is assigned in (d). In the final operation at (e), "/e:0:1=:N" first expands "C1CO1" of vertex index, $v_i=0$. In this example, vertex indexes 0, 1 and 2 are assigned to C, C and O in C1CO1 and the remaining atoms are relabeled with new vertex indexes so that each atom can have its unique vertex index. The nitrogen "N" of vertex index, $v_i=8$ is connected to C of vertex index, $v_i$=1 with a double bound at (e). Note: "e", ":" and "I" are separators used to clarify/identify each component within an operation and between operations, where "e" can represent an expansion.

Applying an operation may involve labeling and relabeling vertex indexes. An approach based on McKay's graph generation algorithm is one embodiment to perform this step. Additionally, the set of substructures used in the operations needs to be predefined. An embodiment for automatically finding a set of substructions is to extract them from training data on molecules. In various situations, a local vertex index is assigned. An embodiment provides enumeration of all atoms in a substructure and assigns a unique vertex index to each atom inside that substructure.

In various embodiments, each of the vertices are identified as, $v_i$=1 to k.

Figure 3:
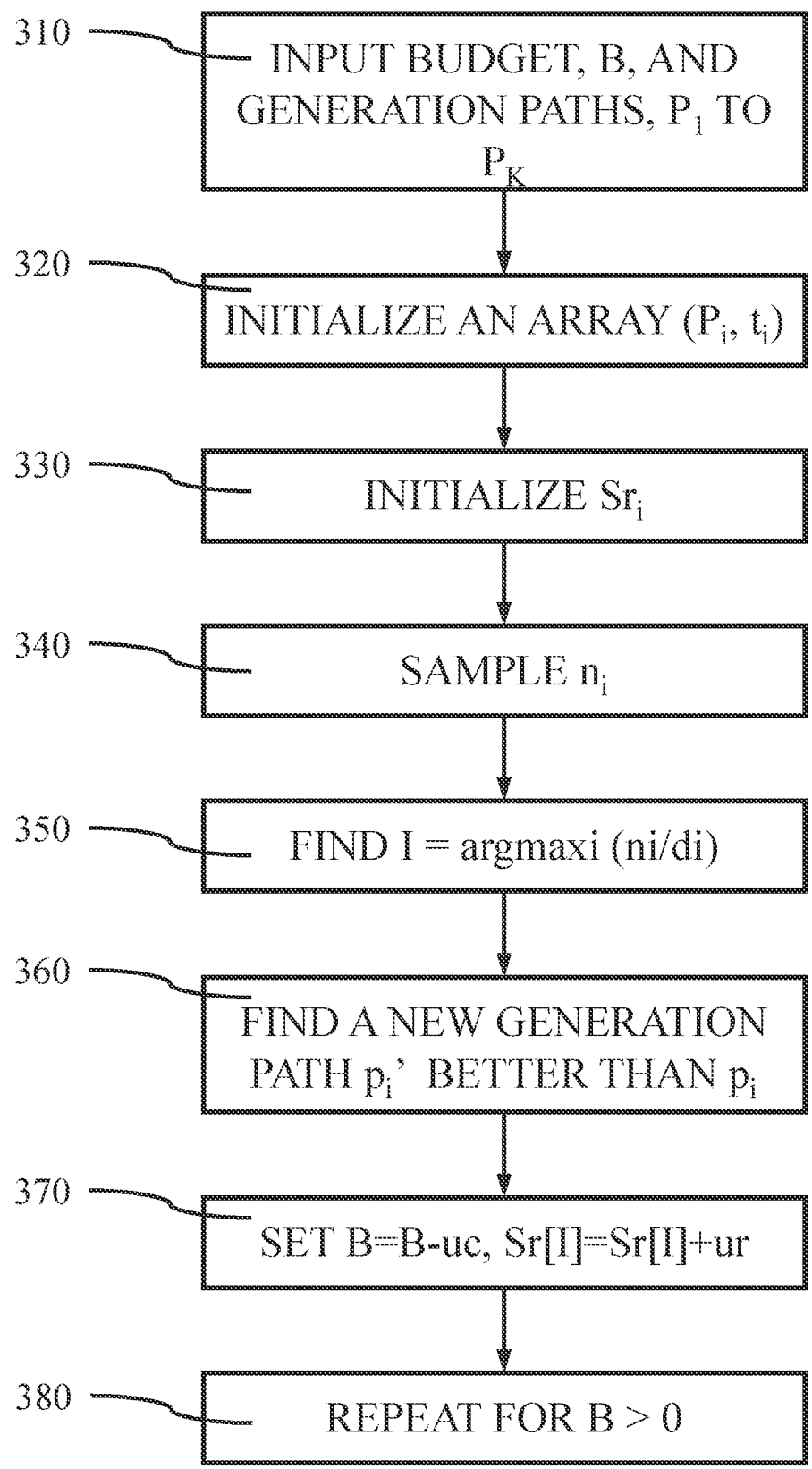
FIG. 3 is a block/flow diagram showing a system/method of a detailed algorithm for molecular optimization of multiple molecules under a limited budget, in accordance with an embodiment of the present invention.

FIG. 3 is a block/flow diagram showing a system/method of a detailed algorithm for molecular optimization of multiple molecules under a limited budget, in accordance with an embodiment of the present invention.

At block 310, a Budget B and generation paths, $P_1$, $P_2$, ... $P_k$, can be inputted to the modification tool, where $P_i$ is the generation path of molecule $m_i$.

At block 320, an array, ($P_i, t_i$), can be initialized, where, for example, ($P_i, t_i$)=[($P_1$,1), ..., ($P_k$,1)], where $t_i$ represents the current threshold for $P_i$, (i.e., $t_i$=1) in the example. A threshold for $t_i$ is defined as the number of operations allowed to change in $P_i$, which can be initially set to 1 (i.e., only one modification is allowed to $P_i$). The value of $t_i$ is updated based on the results of an LDS molecular optimization search.

At block 330, Initialize Sr[i]=Sc[i]=Fr[i]=Fc[i]=0, for i=1, 2, ..., k. (Sr[i],Fr[i]) and (Sc[i], Fc[i]) preserves parameters for the i-th molecule and these parameters are used to perform random samplings over the Beta distribution. In various embodiments, (Sr[i], Fr[i]) are the parameters for the samplings on rewards (bonuses when better molecules are found), while (Sc and Fc) are the parameters for the samplings on the number of times each molecule is selected (or a visit count).

Sr can be initialized with initial objective values if they are already known/easily calculated. An approach to obtain such initial objective values is to call the aforementioned machine-learning-based objective function which receives a molecule as input and returns an objective value of that molecule.

Sample $n_i$ from Beta(Sr[i]+1, Fr[i]+1) and $d_i$ from Beta (Sc[i]+1, Fc[i]+1) for the Beta distribution, where $n_i$ and $d_i$ are random values obtained by the function Beta, which performs the Beta Distribution samplings with parameters (Sr[i]+1, Fr[i]) and (Sc[i]+1, Fc[i]), respectively.

Find $I = \text{argmax}_i(n_i/d_i)$.

Receive (p', t', r) by performing an LDS molecular optimization search that takes as input a chosen generation path $P_I$ and a threshold $t_I$ shown in FIG. 3, where p' is a generation path (if it is found), t' is a new threshold and r is a reward obtained by the LDS molecular optimization search. An LDS molecular optimization search can be performed, which returns a modified generation path (i.e., a modified molecule) obtained by $t_I$ changes to $p_I$.

Set B=B−uc, Sr[I]=Sr[I]+ur, Fr[I]=Fr[I]+u(1−r), Sc[I]=Sc[I]+uc, Fc[I]=Fc[I]+u(1−c), $p_I$=p' and $t_I$=t'. Here, the available computational budget B is decreased, the Beta Distribution parameters for rewards (Sr[I], Fr[I]) for a chosen generation path (i.e., index I) are updated, based on the success/failure of finding a better molecular structure in block 360, and the Beta Distribution parameters for the visit count (Sc[I] and Fc[I]) for the chosen generation path of index I are updated. The generation path $P_I$ and the threshold $t_I$ for the molecule of index I are updated with p' and t' calculated by the LDS molecular optimization search.

"u" is a constant to be able to boost the speed of updating the Beta Distribution parameters (for example, u can be set to 100 in an implementation).

"c" is the cost to pay and is set to be larger if the search effort of the LDS molecular optimization search is computationally more intensive. One embodiment is to define c=N/M (N: the number of nodes expanded by the LDS molecular optimization search, M is a preset constant defined as the maximum number of nodes over which the LDS molecular optimization search is allowed to perform a search.

Another approach is to define $c=(t_I/t_{max})^2$, where $t_{max}$ is a preset constant indicating the maximum threshold value for which the LDS molecule optimization search is allowed. An intuition to set c in this embodiment is based on the fact the LDS molecular optimization search with a larger threshold $t_I$ for molecule of index I is more time-consuming.

At block 380, repeat blocks 340-370 while B>0.

Convert $P_1, P_2, \ldots P_k$ to molecules, order the molecules according to their objective values, and return them with their associated values to the user.

In various embodiments, an LDS-PROBE can be used as one of the procedures in block 320, which is generalized to search in a search tree where an internal node does not necessary have two branches. Starting with the root node, each internal node can have the following branches: one branch to apply an operation without any modification to a generation path and the other branches which either insert, delete or replace one operation there.

Figure 4:
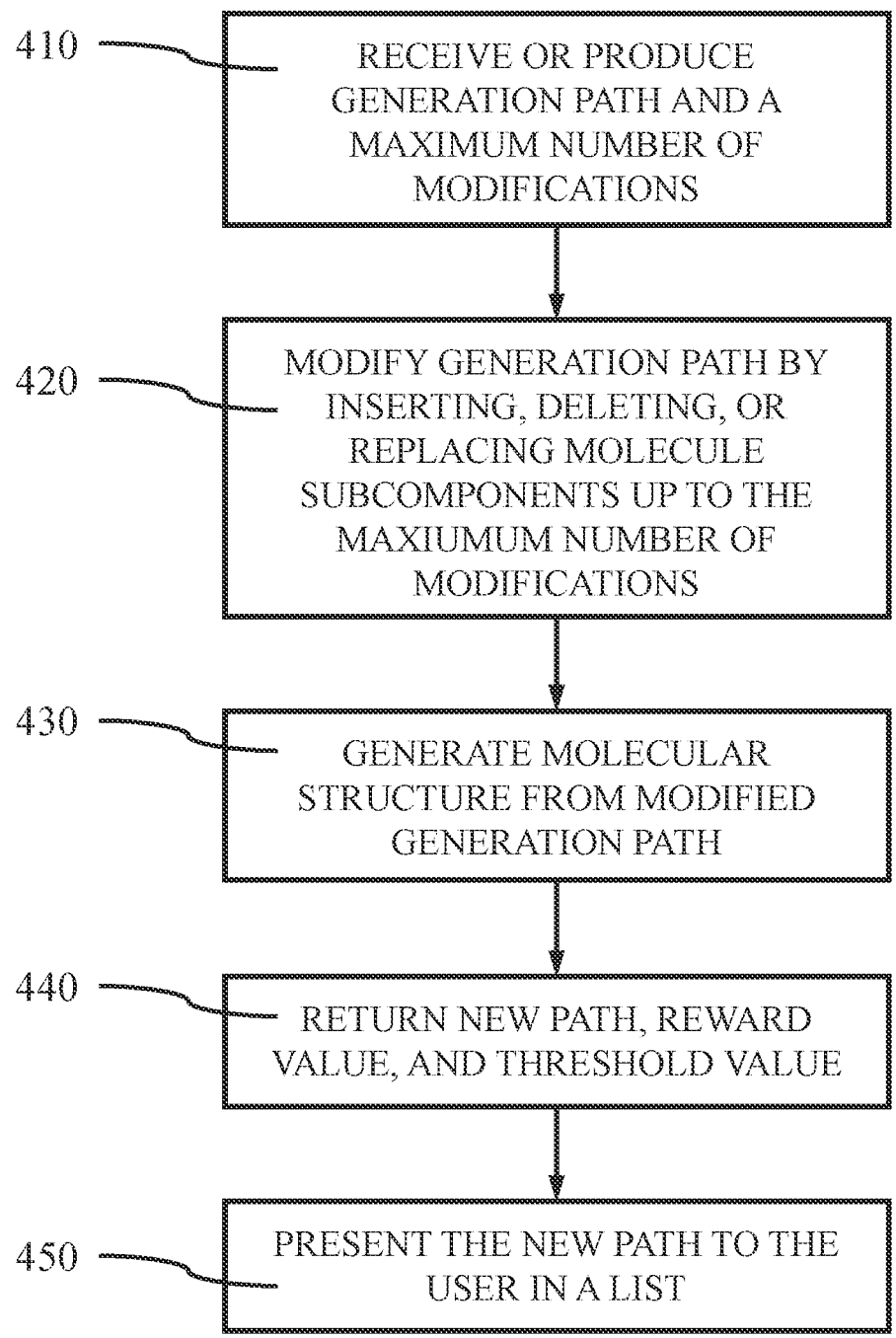
FIG. 4 is a block/flow diagram showing a system/method for modifying a generation path to optimize a molecule, in accordance with an embodiment of the present invention.

FIG. 4 is a block/flow diagram showing a system/method for modifying a generation path to optimize a molecule, in accordance with an embodiment of the present invention.

At block 410, the modification tool can receive a generation path or create a generation path from a molecular structure. A maximum number of modifications per generation path can also be provided by block 360. In various embodiments, the modification tool can receive a generation path p and a threshold t defined as the maximum number of operations/changes allowed to be made top.

At block 420, the generation path of a molecule, $p_i$, can be modified by inserting and deleting operations up to a given number of modifications. Replacing (deleting, then inserting) can be identified as one operation. The number of modifications can be regarded as a distance from the original molecular structure and used as a similarity measure. Updating its generation path within a threshold of the similarity measure to attempt to obtain a molecule that has a molecular structure similar to $p_i$ and that has a better objective value.

At block 430, molecular structures can be generated from the modified generation paths for each molecule and the new molecular structures can be evaluated according to the given objective function.

At block 440 the new path, $p_{new}$, with an associated reward, r, and new threshold, $t_{new}$, can be returned by the tool which receives a generation path $p_i$ and a threshold $t_i$. If the LDS molecular optimization search, which may be allows to make $t_i$ changes, finds a new path $p_{new}$, which is different from $p_i$ and which has a better objective value than that of $p_i$, then $t_{new}$ is set to 1. Setting $t_{new}$=1 indicates that the LDS molecular optimization search will examine molecules with the threshold of 1, expecting that a better molecule will be found with a small amount of computational overhead, if $p_{new}$ is selected later in block 350. The reward is set to $r=1/t_i^2$ to encourage reselection of the case that a better molecule is obtained with a smaller threshold. If the LDS molecular optimization search fails to find a new generation path with threshold $t_i$, then $p_{new}$ is set to $p_i$, that is no change is made to the generation path) and $t_{new}$ is set to $t_i+1$. Setting $t_{new}=t_1+1$ allows the LDS molecular optimization search to search for a molecule which is less similar to $p_i$, but which has a better objective value than that of $p_i$, if $p_i$ is selected again in block 350. The reward is set to $r=0$, thereby reducing the probability of selecting $p_i$ in block 350, since the tool would then need to spend more time finding a better molecule.

If a user has identified sub-structures (e.g., active parts) of the selected molecules as structural constraints, the tool can optimize the molecules while satisfying the constraints (e.g., simplifying only supporting sub-structures).

At block 450 the new path, $p_{new}$, with an associated reward, r, and new threshold, $t_{new}$, can be presented to the user in a list of optimized molecules. The list can be ordered based on the objective values associated with each molecular structure/new path. The user can then select candidate molecules from the provided list of structures and values.

Figure 5:
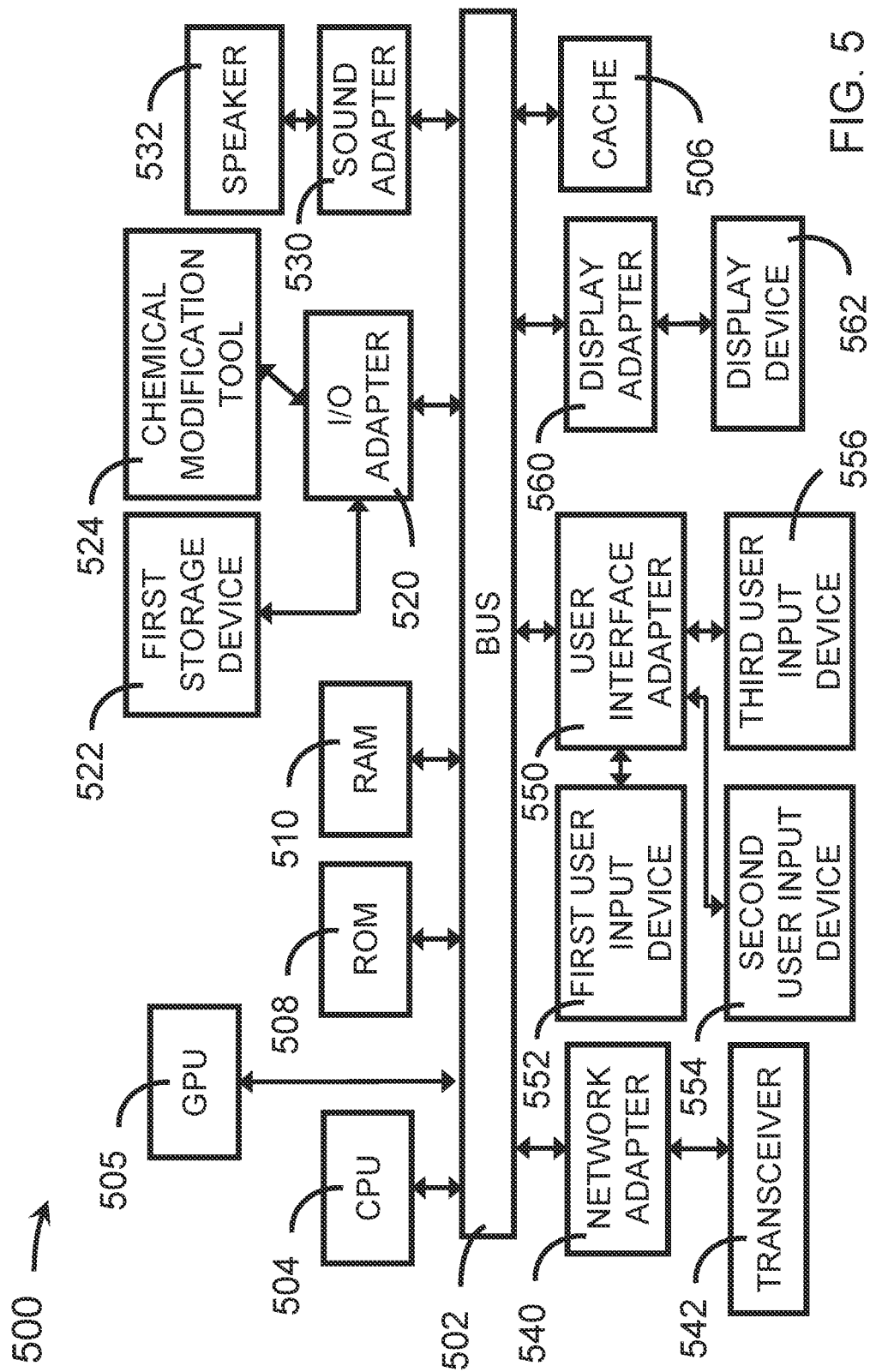
FIG. 5 is an exemplary processing system to which the present methods and systems may be applied, in accordance with an embodiment of the present invention.

FIG. 5 is an exemplary processing system to which the present methods and systems may be applied, in accordance with an embodiment of the present invention.

The processing system 500 can include at least one processor (CPU) 504 and may have a graphics processing (GPU) 505 that can perform vector calculations/manipulations operatively coupled to other components via a system bus 502. A cache 506, a Read Only Memory (ROM) 508, a Random Access Memory (RAM) 510, an input/output (I/O) adapter 520, a sound adapter 530, a network adapter 540, a user interface adapter 550, and/or a display adapter 560, can also be operatively coupled to the system bus 502.

A first storage device 522 and a second storage device 524 are operatively coupled to system bus 502 by the I/O adapter 520, where a tool for molecular optimization can be stored for implementing the features described herein. The storage devices 522 and 524 can be any of a disk storage device (e.g., a magnetic or optical disk storage device), a solid state storage device, a magnetic storage device, and so forth. The storage devices 522 and 524 can be the same type of storage device or different types of storage devices. The chemical modification tool that optimizes molecules 100 can be stored in the storage device 524 and implemented by the at least one processor (CPU) 504 and/or the graphics processing (GPU) 505.

A speaker 532 can be operatively coupled to the system bus 502 by the sound adapter 530. A transceiver 542 can be operatively coupled to the system bus 502 by the network adapter 540. A display device 562 (e.g., computer monitor) can be operatively coupled to the system bus 502 by display adapter 560.

A first user input device 552, a second user input device 554, and a third user input device 556 can be operatively coupled to the system bus 502 by the user interface adapter 550. The user input devices 552, 554, and 556 can be any of a keyboard, a mouse, a keypad, an image capture device, a motion sensing device, a microphone, a device incorporating the functionality of at least two of the preceding devices, and so forth. Of course, other types of input devices can also be used, while maintaining the spirit of the present principles. The user input devices 552, 554, and 556 can be the same type of user input device or different types of user input devices. The user input devices 552, 554, and 556 can be used to input and output information to and from the processing system 500.

In various embodiments, the processing system 500 may also include other elements (not shown), as readily contemplated by one of skill in the art, as well as omit certain elements. For example, various other input devices and/or output devices can be included in processing system 500, depending upon the particular implementation of the same, as readily understood by one of ordinary skill in the art. For example, various types of wireless and/or wired input and/or output devices can be used. Moreover, additional processors, controllers, memories, and so forth, in various configurations can also be utilized as readily appreciated by one of ordinary skill in the art. These and other variations of the processing system 500 are readily contemplated by one of ordinary skill in the art given the teachings of the present principles provided herein.

Moreover, it is to be appreciated that system 500 is a system for implementing respective embodiments of the present methods/systems. Part or all of processing system 500 may be implemented in one or more of the elements of FIGS. 1-4. Further, it is to be appreciated that processing system 500 may perform at least part of the method(s) described herein including, for example, at least part of the method(s) of FIGS. 1-4.

Embodiments described herein may be entirely hardware, entirely software or including both hardware and software elements. In a preferred embodiment, the present invention is implemented in software, which includes but is not limited to firmware, resident software, microcode, etc.

Embodiments may include a computer program product accessible from a computer-usable or computer-readable medium providing program code for use by or in connection with a computer or any instruction execution system. A computer-usable or computer readable medium may include any apparatus that stores, communicates, propagates, or transports the program for use by or in connection with the instruction execution system, apparatus, or device. The medium can be magnetic, optical, electronic, electromagnetic, infrared, or semiconductor system (or apparatus or device) or a propagation medium. The medium may include a computer-readable storage medium such as a semiconductor or solid state memory, magnetic tape, a removable computer diskette, a random access memory (RAM), a read-only memory (ROM), a rigid magnetic disk and an optical disk, etc.

Each computer program may be tangibly stored in a machine-readable storage media or device (e.g., program memory or magnetic disk) readable by a general or special purpose programmable computer, for configuring and controlling operation of a computer when the storage media or device is read by the computer to perform the procedures described herein. The inventive system may also be considered to be embodied in a computer-readable storage medium, configured with a computer program, where the storage medium so configured causes a computer to operate in a specific and predefined manner to perform the functions described herein.

A data processing system suitable for storing and/or executing program code may include at least one processor coupled directly or indirectly to memory elements through a system bus. The memory elements can include local memory employed during actual execution of the program code, bulk storage, and cache memories which provide temporary storage of at least some program code to reduce the number of times code is retrieved from bulk storage during execution. Input/output or I/O devices (including but not limited to keyboards, displays, pointing devices, etc.) may be coupled to the system either directly or through intervening I/O controllers.

Network adapters may also be coupled to the system to enable the data processing system to become coupled to other data processing systems or remote printers or storage devices through intervening private or public networks. Modems, cable modem and Ethernet cards are just a few of the currently available types of network adapters.

As employed herein, the term "hardware processor subsystem" or "hardware processor" can refer to a processor, memory, software or combinations thereof that cooperate to perform one or more specific tasks. In useful embodiments, the hardware processor subsystem can include one or more data processing elements (e.g., logic circuits, processing circuits, instruction execution devices, etc.). The one or more data processing elements can be included in a central processing unit, a graphics processing unit, and/or a separate processor- or computing element-based controller (e.g., logic gates, etc.). The hardware processor subsystem can include one or more on-board memories (e.g., caches, dedicated memory arrays, read only memory, etc.). In some embodiments, the hardware processor subsystem can include one or more memories that can be on or off board or that can be dedicated for use by the hardware processor subsystem (e.g., ROM, RAM, basic input/output system (BIOS), etc.).

In some embodiments, the hardware processor subsystem can include and execute one or more software elements. The one or more software elements can include an operating system and/or one or more applications and/or specific code to achieve a specified result.

In other embodiments, the hardware processor subsystem can include dedicated, specialized circuitry that performs one or more electronic processing functions to achieve a specified result. Such circuitry can include one or more application-specific integrated circuits (ASICs), field-programmable gate arrays (FPGAs), and/or programmable logic arrays (PLAs).

These and other variations of a hardware processor subsystem are also contemplated in accordance with embodiments of the present invention.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

Reference in the specification to "one embodiment" or "an embodiment", as well as other variations thereof, means that a particular feature, structure, characteristic, and so forth described in connection with the embodiment is included in at least one embodiment. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This can be extended, as readily apparent by one of ordinary skill in this and related arts, for as many items listed.

The terminology used herein is for the purpose of describing particular embodiments only and is not intended to be limiting of example embodiments. As used herein, the singular forms ""an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements and/or components, but do not preclude the presence or addition of one or more other features, integers, steps, operations, elements, components and/or groups thereof.

Spatially relative terms such as "beneath," "below," "lower," "above," upper," and the like, can be used herein for ease of description to describe one element's or feature's relationship to another element(s) or feature(s) ac illustrated in the FIGS. It will be understood that the spatially relative terms are intended to encompass different orientations of the device in use or operation in addition to the orientation depicted in the FIGS. For example, if the device in the FIGS. is turned over, elements described as "below" or "beneath" other elements or features would then be oriented "above" the other elements or features. Thus, the term "below" can encompass both an orientation of above and below. The device can be otherwise oriented (rotated 90 degrees or at other orientations), and the spatially relative descriptors used herein can be interpreted accordingly. In addition, it will also be understood that when a layer is referred to as being "between" two layers, it can be the only layer between the two layers, or one or more intervening layers can also be present.

It will be understood that, although the terms first, second, etc. can be used herein to describe various elements, these elements should not be limited by these terms. These terms are only used to distinguish one element from another element. Thus, a first element discussed below could be termed a second element without departing from the scope of the present concept.

It will also be understood that when an element such as a layer, region or substrate is referred to as being "on" or "over" another element, it can be directly on the other element or intervening elements can also be present. In contrast, when an element is referred to as being "directly on" or "directly over" another element, there are no intervening elements present. It will also be understood that when an element is referred to as being "connected" or "coupled" to another element, it can be directly connected or coupled to the other element or intervening elements can be present. In contrast, when an element is referred to as being "directly connected" or "directly coupled" to another element, there are no intervening elements present.

Having described preferred embodiments of a system and method (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. A computer implemented method of modifying molecular structures constrained by a budget, comprising:
    receiving from a user a subset of molecules, where each molecule is represented as a generation path;
    receiving from the user an allotted budget, that includes a time constraint, for modifying a selection of molecules from the subset of molecules;
    testing a first molecule;
    reducing the allotted budget based on resources expended to test the first molecule;
    testing a second molecule;
    reducing the allotted budget based on the resources expended to test the second molecule;
    determining a remaining amount of the allotted budget;
    testing additional molecules from the subset of molecules until the allotted budget is exhausted; and
    presenting the tested molecules to the user.

2. The computer implemented method of claim 1, wherein testing the first molecule includes, selecting the first molecule from the subset of molecules; and
    modifying the generation path of the selected first molecule in a manner that changes a chemical, a physical, or a biological property value of the first molecule to be closer to a user defined value; and
    testing the second molecule includes, selecting the second molecule from the subset of molecules; and
    modifying the generation path of the selected second molecule in a manner that changes a chemical, a physical, or a biological property value of the second molecule to be closer to the user defined value; and testing additional molecules includes, selecting the additional molecules from the subset of molecules; and modifying the generation path of each of the selected additional molecule in a manner that changes a chemical, a physical, or a biological property value of the additional molecule to be closer to the user defined value.

3. The computer implemented method of claim 2, wherein the selection of the first molecule, the second molecule, and the additional molecules is formulated as a multi-armed bandit problem, and wherein the first molecule, the second molecule, and the additional molecules are modified using an objective function to generate an objective value.

4. The computer implemented method of claim 3, wherein the objective function is a Ridge Regression model or a Support Vector Regression model.

5. The computer implemented method of claim 3, further comprising updating a generation path for each molecule being modified.

6. The computer implemented method of claim 5, wherein the generation path is modified by inserting, deleting, or replacing a subcomponent of the selected molecule.

7. The computer implemented method of claim 5, wherein a list of modified molecules is presented in a decreasing ordered based on the objective value of each modified molecule.

8. A computer system for modifying molecular structures constrained by a budget, comprising:
one or more processors;
a computer display;
a computer memory operatively coupled to the one or more processors; and
a chemical modification tool stored in the computer memory that is configured to receive from a user a subset of molecules, where each molecule is represented as a generation path;
receive from the user an allotted budget, that includes a time constraint, for modifying a selection of molecules from the subset of molecules;
test a first molecule;
reduce the allotted budget based on the resources expended to test the first molecule;
test a second molecule;
reduce the allotted budget based on the resources expended to test the second molecule;
determine a remaining amount of the allotted budget;
test additional molecules from the subset of molecules until the allotted budget is exhausted; and
present the tested molecules to the user on the computer display.

9. The computer system of claim 8, wherein testing the first molecule includes, selecting the first molecule from the subset of molecules; and
modifying the generation path of the selected first molecule in a manner that changes a chemical, a physical, or a biological property value of the first molecule to be closer to a user defined value; and
testing the second molecule includes, selecting the second molecule from the subset of molecules; and
modifying the generation path of the selected second molecule in a manner that changes a chemical, a physical, or a biological property value of the second molecule to be closer to the user defined value; and
testing additional molecules includes, selecting the additional molecules from the subset of molecules; and
modifying the generation path of each of the selected additional molecule in a manner that changes a chemical, a physical, or a biological property value of the additional molecule to be closer to the user defined value.

10. The computer system of claim 9, wherein the selection of the first molecule, the second molecule, and the additional molecules is formulated as a multi-armed bandit problem, and wherein the first molecule, the second molecule, and the additional molecules are modified using an objective function to generate an objective value.

11. The computer system of claim 10, wherein the objective function is a Ridge Regression model or a Support Vector Regression model.

12. The computer system of claim 10, further comprising updating a generation path for each molecule being modified.

13. The computer system of claim 12, wherein the generation path is modified by inserting, deleting, or replacing a subcomponent of the selected molecule.

14. The computer system of claim 12, wherein a list of modified molecules is presented in a decreasing ordered based on the objective value of each modified molecule.

15. A computer program product for modifying molecular structures constrained by a budget, the computer program product comprising a computer readable storage medium having program instructions embodied therewith, the program instructions are executable by a processor to cause a computer to:
receive from a user a subset of molecules, where each molecule is represented as a generation path;
receive from the user an allotted budget, that includes a time constraint, for modifying a selection of molecules from the subset of molecules;
test a first molecule;
reduce the allotted budget based on resources expended to test the first molecule;
test a second molecule;
reduce the allotted budget based on the resources expended to test the second molecule;
determine a remaining amount of the allotted budget;
test additional molecules from the subset of molecules until the allotted budget is exhausted; and
present the tested molecules to the user on a computer display.

16. The computer program product of claim 15, wherein testing the first molecule includes, selecting the first molecule from the subset of molecules; and
modifying the generation path of the selected first molecule in a manner that changes a chemical, a physical, or a biological property value of the first molecule to be closer to a user defined value; and
testing the second molecule includes, selecting the second molecule from the subset of molecules; and
modifying the generation path of the selected second molecule in a manner that changes a chemical, a physical, or a biological property value of the second molecule to be closer to the user defined value; and
testing additional molecules includes, selecting the additional molecules from the subset of molecules; and
modifying the generation path of each of the selected additional molecule in a manner that changes a chemical, a physical, or a biological property value of the additional molecule to be closer to the user defined value.

17. The computer program product of claim 16, wherein the selection of the first molecule, the second molecule, and the additional molecules is formulated as a multi-armed bandit problem, and wherein the first molecule, the second molecule, and the additional molecules are modified using an objective function to generate an objective value.

18. The computer program product of claim 17, wherein the objective function is a Ridge Regression model or a Support Vector Regression model.

19. The computer program product of claim 18, wherein the program instructions are further cause the computer to update a generation path for each molecule being modified.

20. The computer program product of claim 19, wherein a list of modified molecules is presented in a decreasing ordered based on the objective value of each modified molecule.

\* \* \* \* \*